US010829640B2

(12) United States Patent
Beyer et al.

(10) Patent No.: US 10,829,640 B2
(45) Date of Patent: Nov. 10, 2020

(54) CURABLE HIGH HARDNESS SILICONE COMPOSITION AND COMPOSITE ARTICLES MADE THEREOF

(71) Applicant: Dow Silicones Corporation, Midland, MI (US)

(72) Inventors: Patrick Beyer, Mainz (DE); Yusheng Chen, Shanghai (CN); Shaohui Wang, Shanghai (CN); Hans Peter Wolf, Liederbach (DE)

(73) Assignee: Dow Silicones Corporation, Midland, MI (US)

( * ) Notice: Subject to any disclaimer, the term of this patent is extended or adjusted under 35 U.S.C. 154(b) by 211 days.

(21) Appl. No.: 16/078,370

(22) PCT Filed: Feb. 21, 2017

(86) PCT No.: PCT/CN2017/074233
§ 371 (c)(1),
(2) Date: Aug. 21, 2018

(87) PCT Pub. No.: WO2017/143961
PCT Pub. Date: Aug. 31, 2017

(65) Prior Publication Data
US 2020/0181408 A1 Jun. 11, 2020

(30) Foreign Application Priority Data
Feb. 23, 2016 (CN) .................. PCT/CN2016/074323

(51) Int. Cl.
*C08L 83/04* (2006.01)
*B01J 23/42* (2006.01)
*C08G 77/12* (2006.01)
*C08G 77/20* (2006.01)
*C08K 3/36* (2006.01)
*C08K 5/05* (2006.01)
*C08K 9/04* (2006.01)
*B33Y 70/00* (2020.01)
*B33Y 80/00* (2015.01)

(52) U.S. Cl.
CPC .............. *C08L 83/04* (2013.01); *B01J 23/42* (2013.01); *C08G 77/12* (2013.01); *C08G 77/20* (2013.01); *C08K 3/36* (2013.01); *C08K 5/05* (2013.01); *C08K 9/04* (2013.01); *B01J 2531/828* (2013.01); *B33Y 70/00* (2014.12); *B33Y 80/00* (2014.12); *C08L 2201/00* (2013.01); *C08L 2203/20* (2013.01); *C08L 2205/035* (2013.01); *C08L 2312/00* (2013.01)

(58) Field of Classification Search
CPC ... C08G 77/12; C08G 77/20; C08L 2205/025; B01J 23/40; B01J 23/42; C08K 3/36; B33Y 70/00; B33Y 70/10
See application file for complete search history.

(56) References Cited

U.S. PATENT DOCUMENTS

| 5,077,335 A | 12/1991 | Schwabe et al. |
| 5,403,885 A | 4/1995 | Voigt et al. |
| 5,548,038 A * | 8/1996 | Enami ..................... C08L 83/04 525/478 |
| 5,998,515 A | 12/1999 | Burkus, II et al. |
| 6,037,279 A | 3/2000 | Brookman et al. |
| 6,245,875 B1 | 6/2001 | Wang |
| 6,251,327 B1 | 6/2001 | Bentz et al. |
| 7,271,215 B2 | 9/2007 | Ikeno et al. |
| 2007/0009748 A1 | 1/2007 | Takanami et al. |
| 2007/0106016 A1 | 5/2007 | Zhu |
| 2008/0033120 A1 | 2/2008 | Yoshitake et al. |
| 2009/0275688 A1 | 11/2009 | Sekiba |
| 2010/0012902 A1 | 1/2010 | Rapson |
| 2010/0168276 A1 | 7/2010 | Pottier et al. |

(Continued)

FOREIGN PATENT DOCUMENTS

| CN | 1845968 A | 10/2006 |
| EP | 0251435 A1 | 1/1988 |

(Continued)

OTHER PUBLICATIONS

Machine assisted English translation of JP2006083392A obtained from https://patents.google.com on Feb. 12, 2020, 8 pages.
English abstract and machine assisted translation for JP2009215420 (A), extracted from http://www.worldwide.espacenet.com database on Aug. 13, 2018, 22 pages.
Anders Karlsson, "New Analytical Methods for Silicone Elastomers Used in Drug Delivery Systems", Department of Polymer Technology Royal Institute of Technology, Stockholm 2003, 107 pages.
Walter Noll, "Chemistry and Technology of Silicones", dated 1968, Chapter 1, pp. 1-9.
International Search Report for PCT/CN2017/074233, dated May 25, 2017, 3 pages.

*Primary Examiner* — Kuo Liang Peng
(74) *Attorney, Agent, or Firm* — Warner Norcross + Judd LLP

(57) ABSTRACT

A liquid curable silicone elastomer composition is disclosed. The composition comprises: an organopolysiloxane (A) comprising: an organopolysiloxane (A1) containing at least 2 alkenyl groups bonded to silicon atom per molecule and having a total alkenyl content of from 0.01 to 1.5 mmol/g, and an organopolysiloxane (A2) containing at least 2 alkenyl groups bonded to silicon atom per molecule and having a total alkenyl content of from 5.0 to 15.0 mmol/g; an organopolysiloxane (B) comprising an organopolysiloxane (B1) containing at least 2 silicon-bonded hydrogen atoms per molecule provided by siloxy units of the type $(R_2HSiO_{1/2})x$ where R is independently selected from hydrogen, an aliphatic a hydrocarbyl, an aromatic hydrocarbyl, or an organyl group and $x \geq 2$; a platinum based catalyst (C); an inhibitor (D) selected from the group consisting of acetylenic alcohols and their derivatives; and a silica filler (E).

20 Claims, No Drawings

(56) References Cited

U.S. PATENT DOCUMENTS

2012/0065343 A1 3/2012 Bahadur et al.
2013/0331499 A1 12/2013 Hamamoto et al.
2014/0367723 A1 12/2014 Yamazaki et al.
2015/0001569 A1 1/2015 Yoshitake et al.
2016/0230005 A1 8/2016 Mayumi et al.
2019/0055362 A1 2/2019 Igarashi

FOREIGN PATENT DOCUMENTS

| | | |
|---|---|---|
| EP | 0577276 A2 | 1/1994 |
| EP | 1060217 B1 | 12/2000 |
| EP | 2878640 A1 | 6/2015 |
| JP | H05194860 A | 8/1993 |
| JP | 2005162859 A | 6/2005 |
| JP | 2006083392 A | 3/2006 |
| JP | 2009215420 A | 9/2009 |
| JP | 2012528231 A | 11/2012 |
| JP | 2013159670 A | 8/2013 |
| JP | 2013159671 A | 8/2013 |
| JP | 2013253206 A | 12/2013 |
| JP | 2017145364 A | 8/2017 |
| WO | 2008056810 A1 | 5/2008 |
| WO | 2009017251 A1 | 2/2009 |
| WO | 2010087522 A1 | 8/2010 |
| WO | WO2013137473 A1 | 9/2013 |
| WO | 2014108364 A1 | 7/2014 |
| WO | 2015107333 A1 | 7/2015 |
| WO | 2015056483 A1 | 3/2017 |

\* cited by examiner

CURABLE HIGH HARDNESS SILICONE COMPOSITION AND COMPOSITE ARTICLES MADE THEREOF

CROSS-REFERENCE TO RELATED APPLICATIONS

This application is the National Stage of International Application No. PCT/CN2017/074233 filed on 21 Feb. 2017, which claims priority to and all advantages of PCT Patent Application No. PCT/CN2016/074323 filed on 23 Feb. 2016, the content of which is hereby incorporated by reference.

The present invention relates to silicone elastomers having hardness ≥75 Shore A and liquid curable silicone elastomer compositions producing said silicone elastomers. Also included are articles and composite parts comprising said high hardness (durometer) silicone elastomers.

Liquid curable silicone elastomer compositions typically cure or react to provide for cured silicone elastomers, also referred to as silicone rubbers. The terms silicone rubber and silicone elastomer may be used interchangeably. Liquid curable silicone elastomer compositions include platinum cured silicone elastomers (addition reaction, otherwise known as hydrosilylation). The terms durometer and hardness may also be used interchangeably.

Cured silicone elastomers may be found in a wide variety of applications such as automotive applications; electronics; electric connectors; medical devices and healthcare applications; cooking, baking, and food storage products; infant products such as bottle nipples; apparel such as undergarments, sportswear, and footwear; and in home repair and hardware.

In some instances, the silicone elastomer may be over-moulded onto other parts made of different or same materials, such as metal, plastic, thermoplastic; or may be coated on textile or fabric. For example a silicone gasket can be moulded onto a thermoplastic housing, made from polyamide or polybutylene terephthalate. In another example a wearable electronic device can be obtained by overmoulding a hard thermoplastic such as polycarbonate with a soft layer or part made of liquid silicone rubber.

Organopolysiloxanes may generally be described as polymers having multiple units of the formula (I):

$$R_aSiO_{(4-a)/2} \qquad (I)$$

in which R is independently selected from hydrogen, aliphatic hydrocarbyl, aromatic hydrocarbyl, or organyl group (that is any organic substituent group, regardless of functional type, having one free valence at a carbon atom). Saturated aliphatic hydrocarbyls are exemplified by, but not limited to alkyl groups such as methyl, ethyl, propyl, pentyl, octyl, undecyl, and octadecyl and cycloalkyl groups such as cyclohexyl. Unsaturated aliphatic hydrocarbyls are exemplified by, but not limited to, alkenyl groups such as vinyl, allyl, butenyl, pentenyl, cyclohexenyl and hexenyl; and by alkynyl groups. Aromatic hydrocarbon groups are exemplified by, but not limited to, phenyl, tolyl, xylyl, benzyl, styryl, and 2-phenylethyl. Organyl groups are exemplified by, but not limited to, halogenated alkyl groups such as chloromethyl, 3-chloropropyl, and 3,3,3-trifluoropropyl; nitrogen containing groups such as amino groups, amido groups, imino groups, imido groups; oxygen containing groups such as polyoxyalkylene groups, carbonyl groups, alkoxy groups and hydroxyl groups. Further organyl groups may include sulfur containing groups, fluor containing groups, phosphorus containing groups, boron containing groups. The subscript "a" is an integer of from 0 to 3.

Siloxy units may be described by a shorthand (abbreviated) nomenclature, namely-"M," "D," "T," and "Q", when R is a methyl group (further teaching on silicone nomenclature may be found in Walter Noll, *Chemistry and Technology of Silicones*, dated 1962, Chapter I, pages 1-9). The M unit corresponds to a siloxy unit where a=3, that is $R_3SiO_{1/2}$; the D unit corresponds to a siloxy unit where a=2, namely $R_2SiO_{2/2}$; the T unit corresponds to a siloxy unit where a=1, namely $RSiO_{3/2}$; the Q unit corresponds to a siloxy unit where a=0, namely $SiO_{4/2}$.

Liquid silicone rubber compositions producing silicone rubbers having hardness (or durometer) in the range of 70-80 Shore A are known, and are widely used in consumer articles such as cooking ware, cake moulds, etc. Shore A durometer is typically measured using ASTM D2240-15. The terms hardness and durometer will be used interchangeably in the scope of the present invention.

The Shore A scale is most common for soft elastomeric materials, while the Shore D scale is used for harder materials such as plastics. A range of 80-90 Shore A typically corresponds to about 30-40 Shore D.

Silicone rubbers having hardness >70 Shore A may be achieved from liquid curable silicone rubbers, but also from another class of silicone rubbers, that is, high consistency silicone rubbers (HCR). These high consistency silicone rubbers may be distinguished from liquid silicone rubbers by the type of alkenyl functional polymer used. Typically, HCR are based on alkenyl functional polymers having a degree of polymerization typically >5000, while liquid silicone rubbers are based on alkenyl functional siloxanes having a degree of polymerization <1500 or <1000. Typically, the alkenyl functional polymers in HCR are referred to as gums, and are characterized by their Williams plasticity, in the range of from 0.100 to 0.255 cm, as measured by ASTM D-926-08. A further distinction lies in the type of cure involved for HCR, which may be catalyzed by either platinum based catalyst or more commonly peroxide catalyst. Use of peroxide often requires a mandatory post-curing step to remove cure by-products. Typically, HCR are extruded or moulded. Typically, liquid silicone rubbers, contrary to HCR, are known to allow for injection moulding, while offering fast vulcanization and ease of processing benefits.

U.S. Pat. No. 6,245,875 discloses silicone elastomer composition (HCR) which has hardness of 80 durometer Shore A, low structuring and low specific gravity.

JP2009215420A discloses a composition giving high hardness silicone rubber and semiconductor device using the same as sealing agent.

U.S. Pat. No. 7,271,215 discloses silicone rubber compositions cured into products having a hardness of at least 75 as measured by a type-A durometer and an elongation at break of at least 200%. The silicone rubber compositions of U.S. Pat. No. 7,271,215 contain an organopolysiloxane containing at least two Si-bonded vinyl groups only in side chains on a backbone thereof and having a viscosity of from 0.1 to 100 Pa·s at 25° C., the amount of siloxane units having the vinyl groups being from 2 to 20 mole % of the total siloxane units of organopolysiloxane (B).

U.S. Pat. No. 5,077,335 discloses that organopolysiloxanes containing 0.5 to 11.6 mmol vinyl/g are employed as inhibitors of platinum cure.

Hardness of silicone rubbers >75 Shore A may be achieved by different methods, including but not limited to increased filler loading, increased crosslink densities, mandatory post cure treatment. Several drawbacks may exist, such as viscosity >1000 Pa·s when increased filler loading are used or reduced curing rates or reduced mechanical strength when increased crosslink densities are used.

In some events, high durometer liquid silicone rubbers in the range of 70-80 Shore A come with inherent limitations such as viscosities in excess of 1000 Pa·s and higher (at a shear-rate of 10 s$^{-1}$) which will have a negative impact on the injection moulding process; cure times such as Tc10 >120 seconds and/or Tc90 >240 seconds also having negative impacts on both productivity and final product performance after demoulding; need for postcure adding an additional procedural step; and limited mechanical strength (such as elongation at break, tensile strength and tear resistance).

The Tc10 is defined in the present invention as the time to reach 10% of the maximum torque at 120° C., and Tc 90 is defined in the present invention as the time to reach 90% of the maximum torque at 120° C., as measured by a moveable die rheometer (MDR) at 120° C.

A post cure step is indeed sometimes required to finalize the cure after the object was removed from the mold. Such post cure step may include a residence time of several hours in a heated oven.

Liquid silicone rubber compositions that combine a good processability in injection moulding processes, with a viscosity <1000 Pa·s, cure times of Tc10<60 seconds and Tc90<120 seconds (as measured by a Movable Die Rheometer (MDR) at 120° C.), producing silicone rubbers having durometers 75 Shore A without post cure, remain a technical gap. Indeed, such combination of viscosity and cure times offer good processing conditions for injection moulding, producing silicone rubbers of hardness 75 Shore A without post cure.

The present invention relates to a liquid curable silicone elastomer composition comprising an organopolysiloxane (A) comprising
organopolysiloxane (A1) containing at least 2 alkenyl groups bonded to silicon atom per molecule and having a total alkenyl content of from 0.01 to 1.5 mmol/g, and
organopolysiloxane (A2) containing at least 2 alkenyl groups bonded to silicon atom per molecule and having a total alkenyl content of from 5.0 to 15.0 mmol/g;
an organopolysiloxane (B) comprising
organopolysiloxane (B1) containing at least 2 silicon-bonded hydrogen atom (SiH) per molecule, wherein said silicon-bonded hydrogen atoms are provided in the form of siloxy units of the type $(R_2HSiO_{1/2})_x$ where R is independently selected from hydrogen, aliphatic hydrocarbyl, aromatic hydrocarbyl, or organyl group and x≥2; and
optional organopolysiloxane (B2) containing at least 2 silicon-bonded hydrogen atom per molecule, wherein said silicon-bonded hydrogen atoms are provided in the form of siloxy units of the type $(RHSiO_{2/2})_z$, where R is as described above, and z ≥2;
wherein the molar amount of silicon-bonded hydrogen in the form of siloxy units of the type $(R_2HSiO_{1/2})_x$ is >40 mol % of the total silicon-bonded hydrogen atoms content of organopolysiloxane (B);
a platinum based catalyst (C),
an inhibitor (D) selected from the group consisting of acetylenic alcohols and their derivatives,
a silica filler (E).

The present invention further relates to a process for preparing a cured silicone elastomer from the liquid curable silicone elastomer composition, and to cured silicone elastomer articles and composite parts obtained therefrom.

Also disclosed is a method for increasing hardness of a silicone elastomer by providing for a curable composition comprising an organopolysiloxane (A) comprising
organopolysiloxane (A1) containing at least 2 alkenyl groups bonded to silicon atom per molecule and having a total alkenyl content of from 0.01 to 1.5 mmol/g, and
organopolysiloxane (A2) containing at least 2 alkenyl groups bonded to silicon atom per molecule and having a total alkenyl content of from 5.0 to 15.0 mmol/g;
an organopolysiloxane (B) comprising
organopolysiloxane (B1) containing at least 2 silicon-bonded hydrogen atoms per molecule, wherein said silicon-bonded hydrogen atoms are provided in the form of siloxy units of the type $(R_2HSiO_{1/2})_x$ where R is independently selected from hydrogen, aliphatic hydrocarbyl, aromatic hydrocarbyl, or organyl group and x ≥2; and
optional organopolysiloxane (B2) containing at least 2 silicon-bonded hydrogen atoms per molecule, wherein said silicon-bonded hydrogen atoms are provided in the form of siloxy units of the type $(RHSiO_{2/2})_z$ where R is independently selected from hydrogen, aliphatic hydrocarbyl, aromatic hydrocarbyl, or organyl group and z≥2,
wherein the molar amount of silicon-bonded hydrogen in the form of siloxy units of the type $(R_2HSiO_{1/2})_x$ is >40 mol % of the total silicon-bonded hydrogen atoms content of organopolysiloxane (B);
a platinum based catalyst (C);
an inhibitor (D) selected from the group consisting of acetylenic alcohols and their derivatives;
a silica filler (E).

The amounts of alkenyl groups in the organopolysiloxanes (A1) and (A2) may be measured by NMR and gas chromatography. The amounts of silicon-bonded hydrogen atoms in the organopolysiloxanes (B1) and (B2) may be measured by NMR and infrared spectroscopy (IR). These methods are known to the skilled person and expected to provide results with variations between methods <10% of measuring data. A review of such methods may be found in the thesis of Anders Karlsson, from the Department of Polymer Technology at the Royal Institute of Technology—Stockholm, titled "New Analytical Methods For Silicone Elastomers Used in Drug Delivery Systems", dated 2003, specifically at page 17.

Once available, the weight % of the functional groups of the organopolysiloxanes (A) and (B) may be commuted into mol % by providing for the actual molar weight of the functionality (alkenyl or hydrogen). The value of mol % may then be commuted into mol/g by dividing the mol % value by 100. This number may then be converted into mmol/g (by multiplying by 1000).

The organopolysiloxane (A) comprises organopolysiloxane (A1) and organopolysiloxane (A2).

The organopolysiloxane (A1) may have any structure. The organopolysiloxane (A1) may be a linear, branched or resinous polymer.

The organopolysiloxane (A1) contains at least 2 alkenyl groups bonded to silicon atom per molecule and has a total alkenyl content of from 0.01 to 1.5 mmol alkenyl/g.

Examples of alkenyl groups include vinyl, allyl, butenyl, pentenyl, cyclohexenyl and hexenyl groups. These may be pendent or terminal or at both positions, that is, they may be present on any of the siloxy units of the organopolysiloxane (A1). The organopolysiloxane (A1) may contain at least 3 alkenyl groups bonded to silicon atom per molecule, in either terminal and/or pendent positions.

The viscosity of organopolysiloxane (A1) at 25° C. is typically within a range from 0.1 to 100 Pa·s. Unless otherwise indicated, all viscosities are measured using a rotational viscometer such as a Brookfield viscometer, or by using a capillary rheometer.

The organopolysiloxane (A1) may contain organyl groups such as phenyl groups, fluoro functional group (such as trifluoropropyl groups).

Examples of the organopolysiloxane (A1) which may be used include vinyldimethylsiloxy-endblocked dimethylsiloxane-vinylmethylsiloxane copolymer, vinyldimethylsiloxy-endblocked polydimethylsiloxane, dimethylhydroxysiloxy-endblocked dimethylsiloxane-vinylmethylsiloxane copolymer, and mixtures thereof.

The organopolysiloxane (A1) may be provided either as a single polymer, or as a combination of two or more different polymers. The organopolysiloxane (A1) may be a linear polymer, comprising more than 95 wt % D siloxy units, based on the total siloxy units, with <5 wt % siloxy units being selected from M, T or Q.

The organopolysiloxane (A1) may alternatively contain 0.01-1.0 mmol/g alkenyl groups, alternatively 0.01-0.6 mmol/g alkenyl groups.

The organopolysiloxane (A1) may be present in the composition in an amount of from 35 to 75 wt %, based on the total weight of the composition.

The organopolysiloxane (A2) contains at least 2 alkenyl groups bonded to silicon atom per molecule and has a total alkenyl content of from 5.0 to 15.0 mmol alkenyl/g.

The organopolysiloxane (A2) may be linear, cyclic, or branched, or any combinations thereof. That is, organopolysiloxane (A2) may be composed of any combination of M, D, T or Q siloxy units. The organopolysiloxane (A2) polymers share the common property of carrying a high number of alkenyl groups, that is, having an alkenyl content of from 5.0 to 15.0 mmol/g.

The organopolysiloxane (A2) may conform to general formula (II)

$$(R_2R''SiO_{1/2})_b(R_3SiO_{1/2})_c(RR''SiO_{2/2})_d(R_2SiO_{2/2})_e (R''SiO_{3/2})_f(RSiO_{3/2})_g(SiO_{4/2})_h \quad (II)$$

where R" is an alkenyl functional group (which includes vinyl, allyl, butenyl, pentenyl, cyclohexenyl and hexenyl groups), and R is as described above, and
where the sum "b+c+d+e+f+g" provides for a total alkenyl content of from 5.0 to 15.0 mmol alkenyl/g.

The organopolysiloxane (A2) may be selected from those compounds having general formula (III)

$$(R_2R''SiO_{1/2})_b(R_3SiO_{1/2})_c(SiO_{4/2})_h \quad (III)$$

where R" is an alkenyl functional group as defined above, and R is as described above, and
where h≥1, b≥2, and c is an integer ≥0, provided b+c=4 when h=1, having a total alkenyl content of from 5.0 to 15.0 mmol alkenyl/g. These compounds may alternatively be referred to as "hyperbranched alkenyl functional polymers" including those structures of average molecular formula $M^{(Vi)}_4Q$ or $M^{(Vi)}_{2n}Q_n$, where Vi=vinyl and n≥1, typically being liquids at room temperature.

Examples of organopolysiloxane (A2) having general formula (III) include a branched polysiloxane of the structure $M^{vi}_xQ_y$, with x/y~2/1, having 6.9 mmol/g alkenyl groups (vinyl).

The organopolysiloxane (A2) may be selected from those cyclic compounds having general formula (IV)

$$(RR''SiO_{2/2})_d(R_2SiO_{2/2})_e \quad (IV)$$

where R" is an alkenyl functional group as defined above, and R is as described above, and
where d≥3 and e≥0 having a total alkenyl content of from 5.0 to 15.0 mmol alkenyl/g.

The organopolysiloxane (A2) having general formula (IV) may be exemplified by methylvinylcyclosiloxane, when R is a methyl group and R" is a vinyl group, and d 3 and e=0.

Examples of organopolysiloxane (A2) having general formula (IV) include tetra(methyl-vinyl)cyclotetrasiloxane, having 11.6 mmol/g alkenyl groups (vinyl).

The organopolysiloxane (A2) may be selected from linear compounds having general formula (V)

$$(RR''SiO_{2/2})_d(R_2SiO_{2/2})_e \quad (IV)$$

where R" is an alkenyl functional group as defined above, and R is as described above, and where the sum of "b+c+d+e" provides for a total alkenyl content of from 5.0 to 15.0 mmol alkenyl/g.

In some instances, R in formulas (II) to (V) may be selected from alkyl groups, alkoxy groups or hydroxyl groups.

The organopolysiloxane (A2) may be selected from those compounds having either general formula (II), general formula (III), general formula (IV), general formula (V), or any combination thereof, provided that organopolysiloxane (A2) has a total alkenyl content of from 5.0 to 15.0 mmol alkenyl/g.

The organopolysiloxane (A2) may alternatively contain of from 5.0 to 13.0 mmol/g alkenyl groups.

The viscosity of organopolysiloxane (A2) at 25° C. is typically within a range from 1 to 20000 mPa·s.

The organopolysiloxane (A2) may be present in the composition in an amount of from 0.5 to 10 wt %, based on the total weight of the composition. In all instances, the organopolysiloxane (A2) is present in the composition in amounts such that the alkenyl concentration of organopolysiloxane (A2) accounts for 25 mol % of the total alkenyl concentration in organopolysiloxane (A), alternatively, for 50 mol % of the total alkenyl concentration in organopolysiloxane (A).

Without wishing to be bound by theory, the inventors are of the opinion that the combination of the alkenyl groups from both organopolysiloxanes (A1) and (A2) allows for a particular structure of the network by providing for a combination of polymers having significantly different alkenyl levels. Such a network may be considered a multimodal network, composed of a fraction of short polymer chains having high density of alkenyl functionalities (organopolysiloxane (A2)) and a larger mass fraction of longer polymer chains having a low density of alkenyl functionalities (organopolysiloxane (A1)).

The organopolysiloxane (B) comprises
organopolysiloxane (B1) containing at least 2 silicon-bonded hydrogen atoms per molecule, wherein said silicon-bonded hydrogen atoms are provided in the form of siloxy units of the type $(R_2HSiO_{1/2})_x$ where R is independently selected from hydrogen, aliphatic hydrocarbyl, aromatic hydrocarbyl, or organyl group and x 2; and optional organopolysiloxane (B2) containing at least 2 silicon-bonded hydrogen atoms per molecule, wherein said silicon-bonded hydrogen atoms are provided in the form of siloxy units of the type $(RHSiO_{2/2})_z$ where R is independently selected from hydrogen, aliphatic hydrocarbyl, aromatic hydrocarbyl, or organyl group and z 2, wherein the molar amount of silicon-bonded hydrogen in the form of siloxy units of the type $(R_2HSiO_{1/2})_x$ is >40 mol % of the total silicon-bonded hydrogen atoms content of organopolysiloxane (B).

The organopolysiloxane (B1), containing at least 2 silicon-bonded hydrogen atoms per molecule, is a branched polymer having general formula (VI)

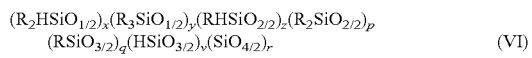  (VI)

where R is as described above (independently selected from hydrogen, aliphatic hydrocarbyl, aromatic hydrocarbyl, or organyl group), and H is hydrogen and
where x≥2, y≥0, z≥0, p≥0, v≥0, and at least one of q or r≥1; alternatively x≥2, y≥0, z≥0, p≥0, q≥0; v≥0, r≥1; alternatively, x≥2, y≥0, r≥1 (with the proviso that when r=1, x+y=4) and z, p, q, v=0. Alternatively, x≥2, y >0, r >1 and z, p, q, v=0.

In all instances, the organopolysiloxane (B1) containing at least 2 silicon-bonded hydrogen atom per molecule, carries the at least 2 silicon-bonded hydrogen atom on the so-called "M" unit, represented by the formula $(R_2HSiO_{1/2})$, also abbreviated $M^H$, indicating one M siloxy unit contains at least 1 silicon-bonded hydrogen atom.

In some instances, the organopolysiloxane (B1) containing at least 2 silicon-bonded hydrogen atom per molecule on the so-called "M" unit, may additionally carry silicon-bonded hydrogen atoms on the so-called D unit, represented by the formula $(RHSiO_{2/2})$, also abbreviated $D^H$, indicating the D siloxy unit contains at least 1 silicon-bonded hydrogen atom.

Methods to obtain the organopolysiloxane (B1) containing at least 2 silicon-bonded hydrogen atom per molecule are known in the art. One example of such method is disclosed in EP0251435, concerned with a method for making siloxane resins containing silicon-bonded hydrogen atoms.

Examples of organopolysiloxane (B1) containing at least 2 silicon-bonded hydrogen atom per molecule include compounds of formula $(R'_2HSiO_{1/2})_x(SiO_{4/2})_r$, where R' is a methyl group, and the ratio x:r ranges of from 0.2:1 to 4:1; in some instances, x may range of from 6 to 10 and r may range of from 3 to 6.

The viscosity of organopolysiloxane (B1) at 25° C. is not critical. The viscosity of organopolysiloxane (B1) at 25° C. may range of from 0.1 to 1000 mPa·s.

The organopolysiloxane (B1) is present in the composition at a level of from 1.0 to 15.0% by weight, based on the total weight of the composition, alternatively of from 1.0 to 10.0% by weight.

The organopolysiloxane (B1) is present in the composition in an amount such that the contribution of organopolysiloxane (B1) is >40 mol % of silicon-bonded hydrogen atoms content relative to the total silicon-bonded hydrogen atoms in organopolysiloxane (B), alternatively >45 mol %, up to 100 mol %. Use of organopolysiloxane (B1) in relative amounts <40 mol % will result in a slow cure of the composition and may also negatively impact hardness of the cured silicone rubber.

The organopolysiloxane (B1) containing at least 2 silicon-bonded hydrogen atom per molecule may be a single compound or a mixture of compounds, where the silicon-bonded hydrogen atoms are found on the so-called M siloxy unit.

The organopolysiloxane (B2) containing at least 2 silicon-bonded hydrogen atom per molecule, is optional and is different from organopolysiloxane (B1). Organopolysiloxane (B2) containing at least 2 silicon-bonded hydrogen atom is typically a polymer bearing the at least 2 silicon-bonded hydrogen atom on D siloxy units.

Organopolysiloxane (B2) containing at least 2 silicon-bonded hydrogen atom per molecule may have general formula (VII)

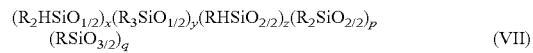  (VII)

where R is as described above,
where x≥0, y >0, z≥2, p≥0, q≥0; alternatively, x=0, y>0, z≥2, p≥0, q≥0.

In all instances, the organopolysiloxane (B2) containing at least 2 silicon-bonded hydrogen atom per molecule carries silicon-bonded hydrogen atoms on D siloxy unit.

In some instances, the organopolysiloxane (B2) containing at least 2 silicon-bonded hydrogen atom per molecule on the D siloxy unit, may additionally carry silicon-bonded hydrogen atoms on the M unit.

The viscosity of organopolysiloxane (B2) at 25° C. may range of from 0.1 to 1000 mPa·s.

The organopolysiloxane (B2) is optionally present in the composition. When present, the organopolysiloxane (B2) is included at a level of from 0.1 to 15.0% by weight, based on the total weight of the composition, alternatively of from 0.1 to 10.0% by weight.

The silicon bonded hydrogen atoms in organopolysiloxane (B) are present in a slight excess from the alkenyl groups in organopolysiloxane (A). The ratio of hydrogen in organopolysiloxane (B)/(alkenyl groups in organopolysiloxane (A) (also SiH/SiAlk ratio) may thus be >1.1, alternatively >1.5, alternatively >1.8.

The presence of the organopolysiloxane (B1) is a critical element of the invention, allowing for overcoming the aforementioned limitations such as slow cure and need for post cure when working with organopolysiloxanes such as organopolysiloxane (A2) having ≥5 mmol/g alkenyl groups, in the hydrosilylation reaction.

By the presence of organopolysiloxane (B1) in conjunction with organopolysiloxane (A2), the hardness of >75 Shore A without post cure is achieved in the resulting cured silicone rubber. By using either one of organopolysiloxane (B1) or organopolysiloxane (A2) in absence of the other, hardness of >75 Shore without post cure cannot be achieved. In the present invention, the combination of (A1) and (A2) with (B1) overcomes the inhibiting property of (A2) such as disclosed in U.S. Pat. No. 5,077,335.

Addition-reaction catalysts are well known in the art. These include catalysts selected form the platinum group metals, or transition metals, of the periodic table of the elements, such as platinum, ruthenium, rhodium, palladium, osmium and iridium; and compounds thereof.

The catalyst used in the scope of the present invention may be selected from the platinum group catalysts, such as chloroplatinic acid, chloroplatinic acid dissolved in an alcohol or a ketone and these solutions which have been ripened, chloroplatinic acid-olefin complexes, chloroplatinic acidalkenylsiloxane complexes, chloroplatinic acid-diketone complexes, platinum black, platinum supported on a carrier, and mixtures thereof.

The catalyst (C) is added in a quantity sufficient to cure the organopolysiloxane (A) and the organopolysiloxane (B) present in the composition. For example, it may be added in a quantity of platinum atom that provides of from 0.1 to 500 weight-ppm (parts per million), alternatively of from 1 to 200 weight-ppm, alternatively of from 1 to 100 weight-ppm, of platinum atom in the catalyst (C) based on the total weight of reactive organopolysiloxanes (A) and (B).

The inhibitors used in the scope of the present invention may be selected from the group consisting of acetylenic alcohols and their derivatives, containing at least one unsaturated bond. Examples of acetylenic alcohols and their derivatives containing at least one unsaturated bond include 1-ethynyl-1-cyclohexanol (ETCH), 2-methyl-3-butyn-2-ol, 3-butyn-1-ol, 3-butyn-2-ol, propargylalcohol, 2-phenyl-2-propyn-1-ol, 3,5-dimethyl-1-hexyn-3-ol, 1-ethynylcyclopentanol, 1-phenyl-2-propynol, 3-methyl-1-penten-4-yn-3-ol, and mixtures thereof.

Alternatively, the inhibitor is selected from the group consisting of 1-ethynyl-1-cyclohexanol, 2-methyl-3-butyn-2-ol, 3-butyn-1-ol, 3-butyn-2-ol, propargylalcohol, 2-phenyl-2-propyn-1-ol, 3,5-dimethyl-1-hexyn-3-ol, 1-ethynylcyclopentanol, 1-phenyl-2-propynol, and mixtures thereof.

Alternatively, the inhibitor is selected from the group consisting of 1-ethynyl-1-cyclohexanol, 2-methyl-3-butyn-2-ol, 3-butyn-1-ol, 3-butyn-2-ol, propargylalcohol, 2-phenyl-2-propyn-1-ol, 1-phenyl-2-propynol, and mixtures thereof.

The inhibitor (D) may be added in the range of from 10 to 10,000 weight-ppm in the curable silicone elastomer composition.

The silica filler suitable for the present invention may have a specific surface area measured by BET method of at least 50 m$^2$/g up to 450 m$^2$/g. Examples of silica filler include precipitated silica (wet silica), fumed silica (dry silica), calcined silica, and the like. The silica filler may be surface-treated, hydrophilic or hydrophobic. The silica may contain alkenyl group on its surface.

In some instances, the silica contains alkenyl group covalently bound to its surface. Methods to provide alkenyl groups on silica are known in the art.

The silica filler is present in the composition in an amount of from 10 to 40% wt based on the total weight of the composition.

Additives may be present in the composition depending on the intended use of the curable silicone elastomer composition. Examples of additives include electrical conductive fillers, thermally conductive fillers, non-conductive filler different from silica filler (E), chain extenders, pot life extenders, flame retardants, pigments, lubricants, adhesion promoters, mold release agents, diluents, solvents, UV light stabilizers, bactericides, wetting agent, heat resistant agent, plasticizer, etc.

Examples of electrical conductive fillers include metal particles, metal oxide particles, metal-coated metallic particles (such as silver plated nickel), metal coated non-metallic core particles (such as silver coated talc, or mica or quartz), carbon nanotube, graphene, and a combination thereof. Metal particles may be in the form of powder, flakes or filaments, and mixtures or derivatives thereof.

Examples of thermally conductive fillers include boron nitride, alumina, metal oxides (such as zinc oxide, magnesium oxide, aluminium oxide), graphite, diamond, and mixtures or derivatives thereof.

Examples of non-conductive fillers, different from silica filler (E), include quartz powder, diatomaceous earth, talc, clay, calcium carbonate, magnesium carbonate, hollow glass, glass fibre, polymer fibres (such as nylon, aramid), hollow resin and plated powder, and mixtures or derivatives thereof.

Examples of pot life extenders include triazole.

Examples of chain extender include straight chain organopolysiloxanes containing 2 silicon-bonded hydrogen groups on the terminal position. Such chain extender is different from any of organopolysiloxane (B1) or organopolysiloxane (B2).

Examples of flame retardants include aluminium trihydrate, chlorinated paraffins, hexabromocyclododecane, triphenyl phosphate, dimethyl methylphosphonate, tris(2,3-dibromopropyl) phosphate (brominated tris), and mixtures or derivatives thereof.

Examples of pigments include iron oxides, carbon black, titanium dioxide, phthalocyanine blue, and mixtures or derivatives thereof.

Examples of lubricants include tetrafluoroethylene, resin powder, graphite, fluorinated graphite, talc, boron nitride, fluorine oil, silicone oil, molybdenum disulfide, and mixtures or derivatives thereof.

Examples of adhesion promoters include silane coupling agents, such as methyltrimethoxysilane, vinyltrimethoxysilane, allyltrimethoxysilane, and 1,6-bis(trimethylsilyl) hexane.

Further additives include silicone fluids, such as trimethylsilyl or OH terminated siloxanes. Such trimethylsiloxy or OH terminated polydimethylsiloxanes typically have a viscosity <150 mPa·s, at 25° C. When present such silicone fluid may be present in the liquid curable silicone elastomer composition in an amount ranging of from 0.1 to 5% weight, based on the total weight of the composition.

The liquid curable silicone elastomer composition may thus comprise
an organopolysiloxane (A) comprising
organopolysiloxane (A1) containing at least 2 alkenyl groups bonded to silicon atom per molecule and having a total alkenyl content of from 0.01 to 1.5 mmol/g, present in an amount of from 35 to 75 wt %, based on the total weight of the composition and
organopolysiloxane (A2) containing at least 2 alkenyl groups bonded to silicon atom per molecule and having a total alkenyl content of from 5.0 to 15.0 mmol/g, present in an amount of from 0.5 to 10.0 wt %, based on the total weight of the composition;
an organopolysiloxane (B) comprising
organopolysiloxane (B1) containing at least 2 silicon-bonded hydrogen atoms per molecule, wherein said silicon-bonded hydrogen atoms are provided in the form of siloxy units of the type $(R_2HSiO_{1/2})_x$ where R is independently selected from hydrogen, aliphatic hydrocarbyl, aromatic hydrocarbyl, or organyl group and x 2, present in an amount of from 1 to 15% by weight, based on the total weight of the composition; and
optional organopolysiloxane (B2) containing at least 2 silicon-bonded hydrogen atoms per molecule, wherein said silicon-bonded hydrogen atoms are provided in the form of siloxy units of the type $(RHSiO_{2/2})_z$ where R is independently selected from hydrogen, aliphatic hydrocarbyl, aromatic hydrocarbyl, or organyl group and z≥2, optionally present in an amount of from 0.1 to 15.0% by weight, based on the total weight of the composition;

wherein the molar amount of silicon-bonded hydrogen in the form of siloxy units of the type $(R_2HSiO_{1/2})_x$ is >40 mol % of the total silicon-bonded hydrogen atoms content of organopolysiloxane (B);

a platinum based catalyst (C) present in an amount of from 0.1 to 500 weight-ppm of platinum atom based on the total weight of reactive organopolysiloxanes (A) and (B);

an inhibitor (D) selected from the group consisting of acetylenic alcohols and their derivatives, present in an amount of from 10 to 10,000 weight-ppm, based on the total weight of the composition;

a silica filler (E), in an amount of from 10 to 40% wt based on the total weight of the composition.

In one embodiment, a process for preparing a cured silicone elastomer comprises
1) forming a mixture of the liquid curable silicone elastomer composition, and
2) curing the mixture at a temperature of from 100 to 220° C.

The liquid curable silicone elastomer composition may readily be prepared in conventional mixing equipment. The order of mixing is not critical if the composition is to be used immediately.

The mixture of the liquid curable silicone elastomer composition may also be prepared by providing for at least 2 separate compositions, such as part I and part II.

In one embodiment, the liquid curable silicone elastomer composition may be provided in at least 2 separate parts.

Part I may contain the catalyst (C) and any one of the organopolysiloxane (A) or the silica filler (E), or a combination of both.

Part II may contain the inhibitor (D) and the organopolysiloxane (B), and any one of the organopolysiloxane (A) or the silica filler (E), or a combination of the latter two.

In some instances, the catalyst (C) is present in a separate part from the organopolysiloxane (B) and the inhibitor (D).

The other or optional additives may be in any of part I or II or in both parts. They may also be added after parts I and II have been combined.

The mixture may be prepared by providing for at least 3 separate parts, such as part I, part II and part III. Parts I and II may be provided as above. Part III may contain any of organopolysiloxane (A), organopolysiloxane (B), the catalyst (C), the inhibitor (D), the silica filler (E) or specific additives such as pigments, filler different from silica filler (E), which may be present as may be required by the final use of the composition.

Subsequently the different parts are combined together and homogeneously mixed, with the optional subsequent step of the addition of any additional additive as may be required by the final use of the composition.

The dynamic viscosity of the final composition may range of from 5 to 1000 Pa·s, alternatively of from 10 to 800 Pa·s, alternatively of from 10 to 500 Pa·s, alternatively of from 50 to 400 Pa·s as measured at room temperature, at a shear rate of 10 s$^{-1}$, using a plate-plate rheometer.

The homogeneous mixing of the components of the present composition may be proceeded to by using a suitable mixing means, such as a spatula, a drum roller, a mechanical stirrer, a three-roll mill, a sigma blade mixer, a bread dough mixer, and a two-roll mill.

The composition may be processed (or cured) by injection moulding, encapsulation moulding, press moulding, dispenser moulding, extrusion moulding, transfer moulding, press vulcanization, centrifugal casting, calendering, bead application or blow moulding.

The composition may alternatively be processed (or cured) using a 3D printing method. A typical method of forming a three-dimensional (3D) article may comprise multiple steps. For example, the method may comprise (i) printing a first heat-curable silicone composition with a 3D printer to form a layer. The method may further comprise (ii) heating the layer to form an at least partially cured layer. In addition, the method may comprise (iii) printing a second heat-curable silicone composition on the at least partially cured layer with the 3D printer to form a subsequent layer. The method may also comprise (iv) heating the subsequent layer to form an at least partially cured subsequent layer. Optionally, steps iii) and iv) may be repeated with independently selected curable silicone composition(s) for any additional layer(s) to form the 3D article. The first and second heat-curable silicone compositions may be the same as or different from one another.

The pot life at 25° C. of the liquid curable silicone elastomer composition is >12 hours, alternatively >24 hours, alternatively >36 hours, alternatively >48 hours, alternatively >72 hours.

The pot life of the present liquid curable silicone elastomer composition is defined as the time to increase mixed viscosity of the composition to 200% of its initial value, as measured by a plate-plate rheometer at a shear-rate of 10 s$^{-1}$, at 25° C. This parameter denotes the minimum processing time.

Curing of the liquid curable silicone elastomer composition may alternatively be carried out a temperature of from 120 to 220° C., alternatively of from 160 to 200° C.

The Tc10 (defined as the time to reach 10% of the maximum torque at 120° C.) is <100 seconds, alternatively <60 seconds.

The Tc90 (defined as the time to reach 90% of the maximum torque at 120° C.) is <150 seconds, alternatively <120 seconds.

The cure monitoring parameters are derived from a movable die rheometer (MDR) experiment using ASTM D5289-92.

Curing can for example take place in a mold to form a moulded silicone article. The composition may for example be injection moulded to form an article, or the composition can be overmoulded or comoulded by injection moulding with a second and different liquid curable silicone elastomer composition of hardness <75 Shore A.

In one embodiment, the present invention relates to a silicone elastomer cured from the liquid curable silicone elastomer composition as described above.

Once cured, the silicone elastomer cured from the liquid curable silicone elastomer composition demonstrates a hardness >75 Shore A without post cure, alternatively >80 Shore A, alternatively >85 Shore A, alternatively >90 Shore A, all without post cure.

Typically, a post cure step may be required to increase hardness, such as a residence time of 4 to 6 hours in a vented oven at a temperature of 200° C. This is not necessary in the scope of the present invention. The present process may thus be free of post curing step.

In one embodiment, the present invention relates to an article cured from the liquid curable silicone elastomer composition. Such articles include those that may be used in producing sports products, diving masks, rubber teats, pacifiers, switch covers, spark-plug connectors, medical products and devices, single-wire seals, plug connector seals, tubing and valves, automobile components such as connector seal and spark plug boots, electric and electronic parts such as rolls in a copying machine and packing in a microwave oven; as well as other products such as feeding bottle nipple and diving gears, in view of the high heat resistance, cold resistance, safety, electric insulation, weatherability, and the like.

In one embodiment, the present invention relates to a composite part comprising a first silicone elastomer cured from the present liquid silicone rubber composition and a second silicone elastomer cured from a second liquid silicone rubber composition, different from the present liquid silicone rubber composition, wherein the second silicone elastomer has a hardness <75 Shore A. Such composite parts include those constructions where a combination of hard and soft elastomers are used, where the first silicone elastomer cured from the present liquid silicone rubber composition is considered as the "hard" elastomer, and the second liquid silicone rubber composition, different from the present liquid silicone rubber composition, is considered the "soft" elastomer. These composite parts may also be referred to as "hard-soft" composites. The present composite part combines the hardness of the first silicone elastomer (hard) per the present invention and the soft feel of the second and different silicone elastomer (soft).

Similar composite parts are those composite parts comprising a plastic or thermoplastic substrate and soft silicone elastomer used as an integral component. In the present instance, the plastic or thermoplastic substrate may thus be replaced by the cured silicone elastomer having hardness >75 Shore A of the present invention.

The present composite may be free of adhesive layer or primer, that is, the first and second silicone elastomer adhere (or covalently bond) to one another upon curing. Curing of the first (hard) and second (soft) silicone elastomer may be simultaneous or subsequent and in any order, that is, any of the hard or soft silicone elastomer may be cured in a first step and the other cured in a subsequent step.

The second "soft" silicone elastomer may be obtained from any typical liquid curable silicone elastomer composition that, when cured, provides a silicone elastomer having a hardness <75 Shore A. Such typical liquid curable silicone elastomer compositions are based on the hydrosilylation of an alkenyl functional siloxane with an organopolysiloxane containing a silicon bonded hydrogen atom. Such typical liquid curable silicone elastomer compositions are known in the art.

The advantages of the present invention is to provide for silicone elastomers of hardness ≥75 Shore A in composite parts, which may replace thermoplastic or plastic materials in several applications, where hardness is required, in conjunction with (i) the excellent thermal stability of silicone elastomers and (ii) a strong covalent bonding at the hard-soft interface.

Such thermal stability is of particular interest where composite parts are exposed to elevated temperatures, such as >200° C. (e.g. in automotive parts), in consumer articles requiring high thermal resistance (e.g. cooking ware), or in consumer applications requiring high bonding strength and durability under aging, heat and humidity conditions.

When considering the present composite parts, an additional advantage is to provide for (ii) a strong covalent bonding at the hard-soft interface by using hydrosilylation cure chemistry for the first and second silicone elastomer compositions.

Examples of such composite parts can be found in various industries including, but not limited to, automotive applications, medical applications, consumer and industrial applications, electronic applications. In automotive applications, this may include housings with a silicone seal or gasket, plugs and connectors, components of various sensors, membranes, diaphragms, climate venting components, and the like. In medical applications composite parts may be used in devices such as masks, goggles, tubing and valves catheters, ostomy appliances, respiratory appliances, feeding appliances, contact lenses, hearing aids, orthotics, prosthesis, and the like. In consumer and industrial applications composite parts may be found in shower heads, bakery ware, spatulas, home appliances, shoes, goggles, sports and leisure articles, diving masks, face masks, pacifiers and other baby articles, feeding accessories, seals and surfaces of white good and other kitchen articles, and the like. Electronic applications may include mobile phone cover seal, mobile phone accessories, precision electronic equipment, electrical switches and switch covers, watches and wristbands, wearable electronic devices, and the like.

In one embodiment, the present invention relates to the use of a liquid curable silicone elastomer composition as described above to make an article as described above and/or a composite part as described above.

The present liquid silicone rubber compositions combine a good processability, with a viscosity below 1000 Pa·s (alternatively <800 Pa·s), a cure speed of Tc10<100 seconds (alternatively <60 seconds) and Tc90<150 seconds (alternatively <120 seconds) (as measured by MDR at 120° C.), high mechanical strength, and durometers 75 Shore A (alternatively >80 Shore A, alternatively >85 Shore A) without post cure.

EXAMPLES

Materials (unless otherwise indicated, all viscosities are measured using a rotational viscometer such as a Brookfield viscometer, or by using a capillary rheometer, at 25° C.):
  Organopolysiloxane A1-1: vinyl terminal polydimethylsiloxane having a viscosity of approximately 53,000 mPa·s having 0.03 mmol/g vinyl group, as measured by NMR or gas chromatography
  Organopolysiloxane A1-2: Vinyl terminal poly(dimethylsiloxane-co-methylvinylsiloxane) having a viscosity of 370 mPa·s having 0.44 mmol/g vinyl group
  Organopolysiloxane A2-1: Tetra(methyl-vinyl)cyclotetrasiloxane $[Si(CH_3)(C_2H_3)O]_4$, having 11.6 mmol/g vinyl group, as per known calculation method.
  Organopolysiloxane A2-2: Branched polysiloxane of the structure $M^{Vinyl}_x Q_y$ with x/y≤4/1, having 8.6 mmol/g vinyl groups (as measured by NMR or gas chromatography), and a viscosity of approximately 20 mPa·s at 25° C.
  Organopolysiloxane A2-4: Branched polysiloxane of the structure $M^{Vinyl}_x Q_y$ with x/y~2/1, having 6.9 mmol/g vinyl groups (as measured by NMR or gas chromatography), and a viscosity of approximately 180 mPa·s at 25° C.
  Organopolysiloxane A2-5: Blend of Methyl-vinyl-cyclosiloxanes, $[Si(CH_3)(C_2H_3)O]_x$, x=3,4,5 in relative amounts of 12:3.5:1, having a total of 11.6 mmol/g vinyl group (as per standard calculation, or as measured by NMR or gas chromatography)
  Comparative Alkenyl Functional Organopolysiloxane: OH terminal methylvinylsiloxane having approximately 4.3 mmol/g vinyl (as measured by NMR or gas chromatography), and a viscosity of 15 mPa·s at 25° C.
  Organopolysiloxane B1: $HMe_2SiO_{0.5}$ capped MHQ resin having 0.97 wt. % H as SiH and a viscosity of 25 mPa·s at 25° C.

Organopolysiloxane B2: $Me_3SiO_{0.5}$ terminal poly(dimethyl-co-methylhydrogen)siloxane having 0.69 wt. % H as SiH and a viscosity of 43.5 mPa·s at 25° C.

Chain extender (optional): $HMe_2SiO_{0.5}$ terminal poly(dimethyl)siloxane having a 0.15 wt % H as SiH and a viscosity of about 11 mPa·s at 25° C.

C: catalyst: Karstedt's catalyst (divinyltetramethyldisiloxane complex of platinum)

D: inhibitor: Ethinyl-cyclohexanol (ETCH)

Additive (optional): OH terminal PDMS with a viscosity of approximately 21 mPa·s at 25° C.

MB1 contains 58.8 parts of a dimethylvinylsiloxy terminated polydimethylsiloxane (A1) having a viscosity of about 55 Pa·s at 25° C., and 31.8 parts of a fumed silica filler (E) having a surface area of approximately 300 $m^2/g$. The silica is hydrophobized and has a vinyl functionalization of approximately 0.170 mmol/g.

MB2 contains 58.8 parts of a dimethylvinylsiloxy terminated polydimethylsiloxane (A1) having a viscosity of about 55 Pa·s at 25° C., and 31.8 parts of a fumed silica filler (E) having a surface area of approximately 300 $m^2/g$. The silica is hydrophobized and has a vinyl functionalization of approximately 0.488 mmol/g.

Evaluation

The tensile/elongation is measured according to DIN 53504 (October 2009). The viscosity of the final liquid curable silicone elastomer composition is measured by plate-plate rheometer at a shear rate of 10 $s^{-1}$ according to DIN 53018 (March 1976). The cure times/speed (Tc10/Tc90) were measured by Movable Die Rheometer at 120° C. according to ASTM D5289-12.

Examples 1 to 3

Examples 1 to 3 are disclosed in Table 1, where the compositions are provided by weight, and results of various parameters are indicated in accordance with the present invention.

By the presence of organopolysiloxane (B1) in conjunction with organopolysiloxane (A2) having a vinyl content in the range of from 5.0 to 15.0 mmol/g, the hardness of >75 Shore A, and actually 80 Shore A, without post cure is achieved in the resulting cured silicone rubber, while ensuring the compositions have a viscosity <1000 Pa·s (actually <500 Pa·s) and cure times of Tc10<100 seconds (actually <60 seconds) and/or Tc 90<150 seconds (actually <120 seconds).

TABLE 1

| Ingredients (wt in g) | Example 1 | Example 2 | Example 3 |
|---|---|---|---|
| Silica masterbatch MB1 | 82.7 | 82.2 | 78.6 |
| Organopolysiloxane A1-1 | 2.40 | 2.35 | |
| Organopolysiloxane A1-2 | 6.81 | 6.81 | 6.81 |
| Organopolysiloxane A2-x | 2.01 | 2.55 | 5.10 |
| Organopolysiloxane B1 | 5.35 | 5.35 | 8.80 |
| Platinum catalyst C | 0.07 | 0.07 | 0.07 |
| Inhibitor D | 0.036 | 0.036 | 0.036 |
| OH terminal PDMS fluid | 0.60 | 0.60 | 0.60 |
| Sum (wt in g) | 100.00 | 100.00 | 100.00 |
| Polymer A2-x | A2-2 | A2-4 | A2-4 |
| vinyl in A2 (mmol/g) | 8.6 | 6.9 | 6.9 |
| PARAMETERS | | | |
| Hardness (Shore A) | 80 | 84 | 90 |
| Elongation (%) | 340 | 227 | 77 |
| Tensile (MPa) | 10.6 | 8.5 | 7.0 |
| Viscosity at 10 $s^{-1}$ (Pa · s) | 342 | 183 | 217 |
| Tc10 at 120° C. (seconds) | 18 | 16 | 19 |
| Tc90 at 120° C. (seconds) | 52 | 80 | 119 |
| vinyl from A2 (mmol/g) | 0.1727 | 0.1747 | 0.3494 |
| total vinyl (mmol/g) | 0.2659 | 0.2679 | 0.4419 |
| A2 relative to total vinyl (%) | 65 | 65 | 79 |
| M(H) content (mmol/g) | 0.5350 | 0.5350 | 0.8800 |
| D(H) content (mmol/g) | 0 | 0 | 0 |
| total SiH (mmol/g) | 0.5350 | 0.5350 | 0.8800 |
| M(H) relative to total SiH (%) | 100 | 100 | 100 |
| SiH/vinyl ratio | 2.01 | 2.00 | 1.99 |

Examples 4 to 7

Examples 4 to 7 are disclosed in Table 2, where the compositions are provided by weight, and results of various parameters are indicated in accordance with the present invention. The compositions are provided by weight, and results of various parameters are indicated.

Examples 4 to 7 rely on the combination of organopolysiloxanes (B1) and (B2), where organopolysiloxane (B1) provides for silicon bonded hydrogen on M units and organopolysiloxane (B2) provides for silicon bonded hydrogen on D siloxy units.

A 50/50 mol % combination of D(H) in organopolysiloxane (B2) and M(H) in organopolysiloxane (B1) is featured in Examples 4 and 5.

Examples 6 and 7 see the presence of a chain extender containing only terminal silicon bonded hydrogen atoms on a linear siloxane (free of Q unit), which was found to positively affect elongation at break, without affecting the hardness.

Example 7 provides for a combination of organopolysiloxane (A2) in accordance with the present invention, where both have a vinyl content is >15 wt %, with a combination of organopolysiloxanes (B1) and (B2) where the molar content of M(H) from organopolysiloxane (B1) is >40 mol % from the total of silicon bonded hydrogen of organosiloxane (B).

The compositions of Examples 4 to 7 are in the scope of the present invention having a viscosity <1000 Pa·s (actually <500 Pa·s) and cure times of Tc10<100 seconds (actually <60 seconds) and/or Tc90<150 seconds (actually <120 seconds), providing for cured silicone rubbers with a hardness of >75 Shore A, and actually 80 Shore A, without post cure.

TABLE 2

| Ingredients (wt in g) | Example 4 | Example 5 | Example 6 | Example 7 |
|---|---|---|---|---|
| Silica masterbatch MB1 | 82.7 | 84.7 | 84.7 | |
| Silica masterbatch MB2 | | | | 79.3 |
| Organopolysiloxane A1-1 | 1.23 | 1.21 | 1.21 | 1.90 |
| Organopolysiloxane A1-2 | 6.81 | 5.24 | 5.24 | 4.92 |
| Organopolysiloxane A2-x | 2.01 | 1.52 | 1.52 | 0.7/2.35 |
| Organopolysiloxane B1 | 2.68 | 2.70 | 2.70 | 6.29 |
| Organopolysiloxane B2 | 3.85 | 3.90 | 3.40 | 2.96 |
| Chain extender | | | 0.50 | 0.94 |
| Platinum catalyst C | 0.07 | 0.12 | 0.12 | 0.08 |
| Inhibitor D | 0.036 | 0.030 | 0.030 | 0.028 |

TABLE 2-continued

| Ingredients (wt in g) | Example 4 | Example 5 | Example 6 | Example 7 |
|---|---|---|---|---|
| OH terminal PDMS fluid | 0.60 | 0.61 | 0.61 | 0.57 |
| Sum (wt in g) | 100.00 | 100.01 | 100.01 | 100.00 |
| Polymer A2-x | A2-2 | A2-5 | A2-5 | A2-5/A2-4 |
| vinyl in A2 (mmol/g) | 8.6 | 11.6 | 11.6 | 11.6/6.9 |
| PARAMETERS | | | | |
| Hardness (Shore A) | 82 | 80 | 80 | 87 |
| Elongation (%) | 243 | 226 | 311 | 114 |
| Tensile (MPa) | 9.3 | 6.7 | 8.5 | 6.3 |
| Viscosity at 10 s$^{-1}$ (Pa·s) | 350 | 290 | 315 | 339 |
| Tc10 at 120° C. (seconds) | 33 | 44 | 47 | 45 |
| Tc90 at 120° C. (seconds) | 72 | 95 | 119 | 99 |
| vinyl from A2 (mmol/g) | 0.1727 | 0.1745 | 0.1745 | 0.2416 |
| total vinyl (mmol/g) | 0.2665 | 0.2623 | 0.2623 | 0.4091 |
| A2 relative to total vinyl (%) | 65 | 67 | 67 | 59 |
| M(H) content (mmol/g) | 0.2675 | 0.2700 | 0.2775 | 0.6430 |
| D(H) content (mmol/g) | 0.2657 | 0.2691 | 0.2346 | 0.2041 |
| total SiH (mmol/g) | 0.5332 | 0.5391 | 0.5121 | 0.8471 |
| M(H) relative to total SiH (%) | 50 | 50 | 54 | 76 |
| SiH/vinyl ratio | 2.00 | 2.06 | 1.95 | 2.07 |

Comparative Examples C1 to C5

Comparative examples are disclosed in Table 3, reviewing the different approaches to target high durometer silicone rubbers according to parameters outside of the scope of the present invention. The compositions are provided by weight, and results of various parameters are indicated.

Comparative example C1 is a typical liquid silicone rubber composition where viscosity <1000 Pa·s and cure times of Tc10<100 seconds and/or Tc 90<150 seconds. Comparative example C1 only uses an organopolysiloxane (B2) having silicon bonded hydrogen on D siloxy units (D(H) groups). Comparative example C1 is thus free of organopolysiloxane (B1) and organopolysiloxane (A2). Hardness (also durometer) is of 66 Shore A, that is, <75 Shore A. Such composition may be considered to provide for the soft part composite discussed above with hardness <75 Shore A.

Comparative example C2 illustrates the approach to use higher filler loadings starting from comparative example C1. Comparative example C2 is also free of organopolysiloxane (B1) and organopolysiloxane (A2). The durometer can reach up to 72 Shore A, but a negative impact is seen on the viscosity of the final composition >1000 Pa·s, unacceptably high for use in injection moulding processes.

Comparative example C3 illustrates another approach to obtain high durometer silicone rubber by using high vinyl concentrations using a comparative polymer to organopolysiloxane (A2) having 4.3 mmol/g alkenyl groups (more than organopolysiloxane (A1), but less than organopolysiloxane (A2)). This approach allows to combine durometer >75 Shore A but <80 Shore A, with acceptable viscosity <1000 Pa·s. A negative impact is seen on the cure times where Tc10 >100 seconds and/or Tc 90 >150 seconds. Comparative example C3 is free of organopolysiloxane (B1) and organopolysiloxane (A2).

Comparative examples C4 calls out on the contribution of both organopolysiloxane (A1) and organopolysiloxane (A2), but without the contribution of organopolysiloxane (B1). This approach allows to combine durometer >75 Shore A but <80 Shore A, with acceptable viscosity <1000 Pa·s. But again, a negative impact is seen on the cure times where Tc10 >100 seconds and/or Tc 90 >150 seconds.

Comparative example C5 illustrates one way to accelerate the cure by using an organopolysiloxane (B1) having silicon bonded hydrogen on M siloxy units (M(H) groups) in a composition according to Comparative example C1, replacing organopolysiloxane (B2). Comparative example C5 is free of organopolysiloxane (A2). The cure is accelerated, but at the same time the durometer is reduced even lower by 4 Shore A (66 Shore A in C1 to 62 Shore A in C6), so the M(H) organopolysiloxane such as organopolysiloxane (B1) is not an obvious choice for high durometer LSR compositions, when used without organopolysiloxane (A2). Such composition may be considered to provide for the soft part composite discussed above with hardness <75 Shore A.

None of these comparative examples allows for the simultaneous combination of durometers >75 Shore A, viscosities <1000 Pa·s and cure times of Tc10<100 seconds and Tc 90<150 seconds.

TABLE 3

| Ingredients (wt in g) | C1 | C2 | C3 | C4 | C5 |
|---|---|---|---|---|---|
| Silica masterbatch MB1 | 82.2 | 82.2 | 80.75 | 82.2 | 82.2 |
| Organopolysiloxane A1-1 | 7.57 | 7.57 | — | 1.12 | 8.42 |
| Organopolysiloxane A1-2 | 6.81 | 6.81 | 6.813 | 6.81 | 6.81 |
| Organopolysiloxane A2-1 (11.6 mmol/g vinyl) | — | — | — | 1.5 | — |
| Comparative Alkenyl Functional Organopolysiloxane (4.3 mmol/g vinyl) | — | — | 4.030 | — | — |
| Organopolysiloxane B1 | — | — | — | — | 1.90 |
| Organopolysiloxane B2 | 2.75 | 2.75 | 7.700 | 7.70 | — |
| Platinum catalyst C | 0.07 | 0.07 | 0.07 | 0.07 | 0.07 |

TABLE 3-continued

| Ingredients (wt in g) | C1 | C2 | C3 | C4 | C5 |
|---|---|---|---|---|---|
| Inhibitor D | 0.036 | 0.036 | 0.036 | 0.036 | 0.036 |
| Additional hydrophobic silica filler | — | 5 | — | — | — |
| OH terminal PDMS fluid | 0.60 | 0.60 | 0.60 | 0.60 | 0.60 |
| Total (wt in g) | 100.0 | 105.0 | 100.0 | 100.0 | 100.0 |
| PARAMETERS | | | | | |
| Hardness(Shore A) | 66 | 72 | 75 | 77 | 62 |
| Elongation (%) | 393 | 400 | 367 | 302 | 414 |
| Tensile (MPa) | 11.2 | 11.6 | 11.4 | 10.4 | 11.6 |
| Viscosity at 10 $s^{-1}$ (Pa·s) | 305 | 1540 | 604 | 393 | 333 |
| Tc10 at 120° C. (seconds) | 64 | 67 | 130 | 230 | 17 |
| Tc90 at 120° C. (seconds) | 127 | 133 | 195 | 381 | 48 |
| vinyl from A2 (mmol/g) | 0 | 0 | 0.1746 | 0.1722 | 0 |
| total vinyl (mmol/g) | 0.0947 | 1 | 0.2665 | 0.2650 | 0.0950 |
| A2 relative to total vinyl (%) | 0 | 0 | 66 | 65 | 0 |
| M(H) content (mmol/g) | 0 | 0 | 0 | 0 | 0.1900 |
| D(H) content (mmol/g) | 0.1898 | 0.1808 | 0.5313 | 0.5313 | 0 |
| total SiH (mmol/g) | 0.1898 | 0.1808 | 0.5313 | 0.5313 | 0.1900 |
| M(H) relative to total SiH (%) | 0 | 0 | 0 | 0 | 100 |
| SiH/vinyl ratio | 2.00 | 2.00 | 1.99 | 2.00 | 2.00 |

The invention claimed is:

1. A liquid curable silicone elastomer composition, said composition comprising:
   an organopolysiloxane (A) comprising;
      an organopolysiloxane (A1) containing at least 2 silicon-bonded alkenyl groups per molecule and having a total alkenyl content of from 0.01 to 1.5 mmol/g, and an organopolysiloxane (A2) containing at least 2 silicon-bonded alkenyl groups per molecule and having a total alkenyl content of from 5.0 to 15.0 mmol/g;
   an organopolysiloxane (B) comprising;
      an organopolysiloxane (B1) containing at least 2 silicon-bonded hydrogen atoms per molecule, wherein the silicon-bonded hydrogen atoms are provided in the form of siloxy units of the type $(R_2HSiO_{1/2})_x$ where R is independently selected from hydrogen, an aliphatic hydrocarbyl, an aromatic hydrocarbyl, or an organyl group and x≥2, and optionally, an organopolysiloxane (B2) containing at least 2 silicon-bonded hydrogen atoms per molecule, wherein the silicon-bonded hydrogen atoms are provided in the form of siloxy units of the type $(RHSiO_{2/2})_z$ where R is independently selected from hydrogen, an aliphatic hydrocarbyl, an aromatic hydrocarbyl, or an organyl group and z≥2, wherein the molar amount of silicon-bonded hydrogen in the form of siloxy units of the type $(R_2HSiO_{1/2})_x$ is >40 mol % of the total silicon-bonded hydrogen atoms content of organopolysiloxane (B);
   a platinum based catalyst (C);
   an inhibitor (D) selected from the group consisting of acetylenic alcohols and their derivatives; and
   a silica filler (E);
   wherein a silicone elastomer cured from the liquid curable silicone elastomer composition has a hardness >75 Shore A without post cure.

2. The liquid curable silicone elastomer composition of claim 1, wherein the organopolysiloxane (A2) is selected from:
   compounds having general formula (II)

$$(R_2R''SiO_{1/2})_b(R_3SiO_{1/2})_c(RR''SiO_{2/2})_d(R_2SiO_{2/2})_e(R''SiO_{3/2})_f(RSiO_{3/2})_g(SiO_{4/2})_h \quad (II)$$

where R" is an alkenyl functional group, and R is independently selected from hydrogen, an aliphatic hydrocarbyl, an aromatic hydrocarbyl, or an organyl group, and where the sum "b+c+d+e+f+g" provides for a total alkenyl content of from 5.0 to 15.0 mmol alkenyl/g; and/or
   compounds having general formula (III)

$$(R_2R''SiO_{1/2})_b(R_3SiO_{1/2})_c(SiO_{4/2})_h \quad (III)$$

where R" is an alkenyl functional group, and R is as described above, and where h≥1, b≥2, and c is an integer ≥0, provided b+c=4 when h=1, having a total alkenyl content of from 5.0 to 15.0 mmol alkenyl/g; and/or
   cyclic compounds having general formula (IV)

$$(RR''SiO_{2/2})_d(R_2SiO_{2/2})_e \quad (IV)$$

where R" is an alkenyl functional group, and R is as described above, and where d≥3 and e≥0 having a total alkenyl content of from 5.0 to 15.0 mmol alkenyl/g; and/or
   linear compounds having general formula (V)

$$(RR''SiO_{2/2})_d(R_2SiO_{2/2})_e \quad (IV)$$

where R" is an alkenyl functional group, and R is as described above, and where the sum "b+c +d+e" provides for a total alkenyl content of from 5.0 to 15.0 mmol alkenyl/g.

3. The liquid curable silicone elastomer composition in accordance with claim 2, wherein the organopolysiloxane (A2) comprises at least one compound having the general formula (II).

4. The liquid curable silicone elastomer composition in accordance with claim 2, wherein the organopolysiloxane (A2) comprises at least one compound having the general formula (III).

5. The liquid curable silicone elastomer composition in accordance with claim 2, wherein the organopolysiloxane (A2) comprises at least one compound having the general formula (IV).

6. The liquid curable silicone elastomer composition in accordance with claim 2, wherein the organopolysiloxane (A2) comprises at least one compound having the general formula (V).

7. The liquid curable silicone elastomer composition in accordance with claim 1, wherein the organopolysiloxane (B1) is a branched polymer having general formula (VI)

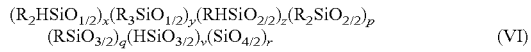
$(R_2HSiO_{1/2})_x(R_3SiO_{1/2})_y(RHSiO_{2/2})_z(R_2SiO_{2/2})_p$
$(RSiO_{3/2})_q(HSiO_{3/2})_v(SiO_{4/2})_r$ (VI)

where R is independently selected from hydrogen, an aliphatic hydrocarbyl, an aromatic hydrocarbyl, or an organyl group, and H is hydrogen, and where $x \geq 2$, $y \geq 0$, $z \geq 0$, $p \geq 0$, $v \geq 0$, and at least one of q or r $\geq 1$.

8. The liquid curable silicone elastomer composition in accordance with claim 1, wherein the organopolysiloxane (B2) is present and has general formula (VII)

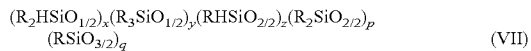
$(R_2HSiO_{1/2})_x(R_3SiO_{1/2})_y(RHSiO_{2/2})_z(R_2SiO_{2/2})_p$
$(RSiO_{3/2})_q$ (VII)

where R is independently selected from hydrogen, an aliphatic hydrocarbyl, an aromatic hydrocarbyl, or an organyl group, and H is hydrogen, and where $x \geq 0$, $y \geq 0$, $z \geq 2$, $p \geq 0$, $q \geq 0$.

9. The liquid curable silicone elastomer composition in accordance with claim 1, wherein the inhibitor (D) is selected from the group consisting of 1-ethynyl-1-cyclohexanol, 2-methyl-3-butyn-2-ol, 3-butyn-1-ol, 3-butyn-2-ol, propargylalcohol, 2-phenyl-2-propyn-1-ol, 3,5-dimethyl-1-hexyn-3-ol, 1-ethynylcyclopentanol, 1-phenyl-2-propynol, 3-methyl-1-penten-4-yn-3-ol, and mixtures thereof.

10. The liquid curable silicone elastomer composition in accordance with claim 1, wherein the silica filler (E) contains at least one alkenyl group covalently bound to its surface.

11. The liquid curable silicone elastomer composition in accordance with claim 1, comprising:
35 to 75 weight % (wt %) of the organopolysiloxane (A1);
0.5 to 10 wt % of the organopolysiloxane (A2);
1 to 15 wt % of the organopolysiloxane (B1);
0.1 to 15 wt % of the organopolysiloxane (B2);
0.1 to 500 weight-ppm (parts per million) of platinum atom in the catalyst (C) based on the total weight of reactive organopolysiloxanes (A) and (B);
10 to 10,000 weight-ppm of the inhibitor (D); and
10 to 40 wt % of the silica filler (E);
except for catalyst (C), on the total weight of the composition.

12. A process for preparing a cured silicone elastomer, said process comprising:
1) forming a mixture of the liquid curable silicone elastomer composition according to claim 1; and
2) curing the mixture at a temperature of from 100 to 220° C.;
optionally, wherein the mixture is formed by providing at least 2 separate compositions.

13. A silicone elastomer cured from the liquid curable silicone elastomer composition according to claim 1.

14. The silicone elastomer of claim 13, having a hardness >75 Shore A, optionally a hardness >80 Shore A, optionally a hardness >85 Shore A.

15. An article cured from the liquid curable silicone elastomer composition according to claim 1.

16. The article of claim 15, selected from the group consisting of sports products, diving masks and gears, feeding bottle nipples and rubber teats, pacifiers, switch covers, spark-plug connectors, medical products and devices, single-wire seals, plug connector seals, tubing and valves, automobile components, and electric and electronic parts.

17. A composite part comprising a first silicone elastomer cured from a first liquid silicone rubber composition, and a second silicone elastomer cured from a second liquid silicone rubber composition which is different from the first liquid silicone rubber composition, wherein the first liquid silicone rubber composition is the liquid silicone rubber composition according to claim 1, and wherein the second silicone elastomer has a hardness <75 Shore A.

18. The composite part of claim 16, selected from the group consisting of housings with a silicone seal or gasket, plugs and connectors, components of sensors, membranes, diaphragms, climate venting components, masks, goggles, tubing and valves, catheters, ostomy appliances, respiratory appliances, feeding appliances, contact lenses, hearing aids, orthotics, prosthesis, shower heads, bakery ware, spatulas, home appliances, shoes, goggles, sports and leisure articles, diving masks, face masks, pacifiers and baby articles, feeding accessories, seals and surfaces of kitchen articles, mobile phone cover seals, mobile phone accessories, precision electronic equipment, electrical switches and switch covers, watches and wristbands, and wearable electronic devices.

19. A method for increasing hardness of a silicone elastomer, said method comprising providing the liquid curable silicone composition according to claim 1.

20. A method of forming a three-dimensional (3D) article, said method comprising:
i) printing a first heat-curable silicone composition with a 3D printer to form a layer;
ii) heating the layer to form an at least partially cured layer;
iii) printing a second heat-curable silicone composition on the at least partially cured layer with the 3D printer to form a subsequent layer;
iv) heating the subsequent layer to form an at least partially cured subsequent layer; and,
v) optionally, repeating steps iii) and iv) with independently selected heat-curable silicone composition(s) for any additional layer(s) to form the 3D article;
wherein the first and second heat-curable silicone compositions are the same as or different from one another; and
wherein at least one of the first and second heat-curable silicone compositions is the liquid curable silicone elastomer composition according to claim 1.

* * * * *